United States Patent
Fernando et al.

(10) Patent No.: US 12,243,225 B2
(45) Date of Patent: Mar. 4, 2025

(54) DETERMINING WHETHER HAIRS ON AN AREA OF SKIN HAVE BEEN TREATED WITH A LIGHT PULSE

(71) Applicant: KONINKLIJKE PHILIPS N.V., Eindhoven (NL)

(72) Inventors: Shakith Devinda Fernando, Eindhoven (NL); Karl Catharina Van Bree, Eindhoven (NL); Jan Brouwer, Eindhoven (NL); Gerben Kooijman, Leende (NL); Felipe Maia Masculo, Eindhoven (NL); Cornelis Willem Hameetman, Rotterdam (NL); Adrienne Heinrich, Taguig (PH)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 394 days.

(21) Appl. No.: 17/637,868

(22) PCT Filed: Sep. 3, 2020

(86) PCT No.: PCT/EP2020/074558
§ 371 (c)(1),
(2) Date: Feb. 24, 2022

(87) PCT Pub. No.: WO2021/052766
PCT Pub. Date: Mar. 25, 2021

(65) Prior Publication Data
US 2022/0277442 A1 Sep. 1, 2022

(30) Foreign Application Priority Data
Sep. 20, 2019 (EP) .................................. 19198816

(51) Int. Cl.
*G06T 7/00* (2017.01)
*A61N 5/06* (2006.01)

(52) U.S. Cl.
CPC .......... *G06T 7/0012* (2013.01); *A61N 5/0617* (2013.01); *G06T 2207/20081* (2013.01); *G06T 2207/30088* (2013.01)

(58) Field of Classification Search
None
See application file for complete search history.

(56) References Cited

U.S. PATENT DOCUMENTS 6,267,771 B1 7/2001 Tankovich
7,309,335 B2 12/2007 Altshuler
(Continued)

FOREIGN PATENT DOCUMENTS

| EP | 0913127 A2 | 5/1999 |
|---|---|---|
| EP | 1031324 A1 | 8/2000 |
| EP | 1523371 A1 | 4/2005 |

OTHER PUBLICATIONS

International Search Report and Written Opinion Dated Nov. 18, 2020 For International Application No. PCT/EP2020/074558 Filed Sep. 3, 2020.

(Continued)

*Primary Examiner* — Leon Flores

(57) ABSTRACT

According to an aspect, there is provided an apparatus for use with a treatment device. The treatment device is configured to apply a light pulse to skin of a subject to perform a treatment operation to hairs on the skin. The apparatus comprises a processing unit configured to receive one or more images of a first area of the skin from an imaging unit, wherein the imaging unit is arranged to obtain images of the skin of the subject; process the one or more images to determine whether the hairs on the first area of the skin have been treated with a light pulse based on a degree of at least one of carbonisation and curling of the hairs on the first area of the skin as shown in the one or more images; and output (Continued)

a first signal indicating whether the hairs on the first area of skin have been treated with a light pulse.

20 Claims, 7 Drawing Sheets

(56) References Cited

U.S. PATENT DOCUMENTS

| | | |
|---|---|---|
| 2002/0049432 A1 | 4/2002 | Mukai |
| 2003/0023235 A1 | 1/2003 | Cense |
| 2006/0116669 A1 | 6/2006 | Dolleris |
| 2008/0161745 A1 | 7/2008 | Stumpp |
| 2010/0016782 A1 | 1/2010 | Oblong |
| 2011/0301441 A1 | 12/2011 | Bandic |
| 2012/0265182 A1 | 10/2012 | Jay |
| 2014/0142471 A1 | 5/2014 | Chambon |
| 2015/0032092 A1 | 1/2015 | Adanny |
| 2018/0189976 A1* | 7/2018 | Kasprzak ............. A61B 5/0077 |

OTHER PUBLICATIONS

Walker, et al: "Intelligent image analysis for image-guided laser hair removal and skin therapy", Proceedings vol. 8207, Photonic Therapeutics and Diagnostics VIII; 820707 (2012).

* cited by examiner (c)

(d)

(e)

DETERMINING WHETHER HAIRS ON AN AREA OF SKIN HAVE BEEN TREATED WITH A LIGHT PULSE

CROSS REFERENCE TO RELATED APPLICATIONS

This application is the U.S. National Phase application under 35 U.S.C. § 371 of International Application No. PCT/EP2020/074558 filed Sep. 3, 2019, which claims the benefit of European Patent Application Number 19198816.1 filed Sep. 20, 2019. These applications are hereby incorporated by reference herein.

FIELD OF THE INVENTION

This disclosure relates to determining whether hairs on an area of skin of a subject have been treated with a light pulse.

BACKGROUND OF THE INVENTION

Techniques for removal of unwanted hairs include shaving, electrolysis, plucking, laser and light therapies (known as photoepilation) and injection of therapeutic anti-androgens. Light-based technologies are also used in other types of dermatological treatments, including hair growth reduction and treating acne.

Through the use of an appropriate configuration of the light energy, i.e. in terms of wavelength, intensity and/or pulse duration (if the light is to be pulsed), selective heating of the hair root and subsequent temporary or permanent damage to the hair follicle can be achieved. Home-use photoepilation devices, for example the Philips Lumea device, use intense pulsed light (IPL) from high intensity light sources, e.g. Xenon flash lamps that produce high output bursts of broad spectrum light.

A photoepilation treatment is characterized by the user of the photoepilation device treating relatively small areas of the skin for the purpose of hair removal. The photoepilation treatment uses intense light to heat melanin in hair and hair roots, which puts the hair follicles into a resting phase, preventing hair re-growth. For effective use of this technology for hair removal, the user must cover a skin region completely. Since this effect is only of limited duration, treatment has to be repeated on a regular basis: typically once every 4 to 8 weeks in the maintenance phase after an initial period of about two months in which treatment is performed once every two weeks.

US 2003/0023235 A1 discloses a device for treating skin by means of light pulses. The device has a processor for determining, from an image of the skin, a color and a dimension of a target object to be treated, e.g. a hair. The processor determines the dose of the light pulses based on said color and dimension.

US 2015/0032092 A1 discloses a system for cosmetic skin procedures using light. The system has a computer that employs information extracted from an image of the skin to determine optimal treatment doses for the light. Said information may comprise skin pigmentation, blemish thickness, hair pigment, or hair length or thickness.

US 2002/0049432 A1 discloses an apparatus for treatment of a skin of a patient by means of a laser beam. The apparatus comprises a detection unit which detects the color of the skin from an image of the skin taken by an imaging element. A control section determines an irradiation condition of the laser beam based on the detected color.

EP 1 523 371 A1 discloses a handpiece for skin tissue treatment by means of a light beam. The handpiece has a sensor, for example a CCD or CMOS camera, to generate information about the target area on the skin tissue, such as particular properties of the skin tissue, hairs and skin disorders and irregularties such as wrinkles, small marks or spots, and blood vessels. The information generated by the sensor is used to control the treatment.

U.S. Pat. No. 6,267,771 B1 discloses a process for inhibiting the growth of hairs on human skin. A contaminant including a dye is applied to the skin such that it infiltrates into the hair ducts and stains the hair follicles. Light having a wavelength absorbed by said dye is applied to the skin, causing heating of the hair follicles and the surrounding tissue feeding the hair follicles. Application of the light is continued at least until the hairs begin to curl.

In a typical photoepilation treatment, the user of the photoepilation device must repeatedly manually position the photoepilation device on the skin and trigger a light pulse in order to cover a full body region (e.g. an arm, a leg, etc.). However, as a photoepilation device typically does not provide any feedback to the user about the areas that have already been treated, and there are little or no user-perceptible changes to the skin or hairs shortly after applying a light pulse, it is difficult for a user to achieve complete coverage of the body region and/or avoid over-treating certain areas of the body region.

Therefore it is desirable to be able to provide ways to determine whether hairs on an area of skin have been treated with a light pulse.

SUMMARY OF THE INVENTION

According to a first aspect, there is provided an apparatus for use with a treatment device. The treatment device is configured to apply a light pulse to skin of a subject to perform a treatment operation to hairs on the skin. The apparatus comprises a processing unit configured to receive one or more images of a first area of the skin from an imaging unit, wherein the imaging unit is arranged to obtain images of the skin of the subject; process the one or more images to determine whether the hairs on the first area of the skin have been treated with a light pulse based on a degree of at least one of carbonisation and curling of the hairs on the first area of the skin as shown in the one or more images; and output a first signal indicating whether the hairs on the first area of skin have been treated with a light pulse. Thus, the apparatus is able to determine whether hairs on an area of skin have been treated with a light pulse from one or more images of the skin area.

In some embodiments the processing unit is configured to determine the degree of carbonisation of the hairs based on a colour of the hairs and/or size of the hairs determined from the one or more images. In some embodiments the processing unit is configured to determine the degree of curling of the hairs based on a degree of curvature of the hairs determined from the one or more images.

In some embodiments the processing unit is configured to determine whether the hairs on the first area of the skin have been treated with a light pulse by comparing the determined degree of said at least one of carbonisation and curling of the hairs on the first area of the skin to respective thresholds for the degree of carbonisation and the degree of curling; or combining the determined degrees of carbonisation and curling of the hairs into a combined degree of carbonisation and curling, and comparing the combined degree of carbonisation and curling to a threshold for the combined degree of carbonisation and curling.

In further or alternative embodiments, the processing unit is configured to use a trained machine learning model to process the one or more images to determine whether the hairs on the first area of the skin have been treated with a light pulse. The trained machine learning model can be an artificial neural network, such as a deep neural network.

In some embodiments the processing unit is further configured to receive one or more further images of the first area of the skin from the imaging unit, wherein the one or more further images are obtained by the imaging unit after a light pulse is applied to the first area of the skin; and update the trained machine learning model using the one or more further images. These embodiments enable the performance of the machine learning model to be refined or improved over time, and in particular the use of images of the subject's skin enables the machine learning model to be calibrated or customized to the skin characteristics of the subject.

In some embodiments the processing unit is further configured to analyze the one or more images to identify parts of the one or more images comprising hairs, and the processing unit is configured to process the identified parts of the one or more images to determine whether the hairs on the first area of the skin have been treated with a light pulse. These embodiments can make the processing of the one or more images more efficient.

In some embodiments the processing unit is further configured to process the one or more images to determine further information about the hairs on the first area of the skin, and to include said further information in the first signal. In these embodiments the further information can comprise at least one of a density of the hairs in the first area of the skin; a strength of the hairs in the first area of the skin; a thickness of the hairs in the first area of the skin; and a colour of the hairs in the first area of the skin.

In some embodiments the first signal comprises the one or more images and an indication of a part or parts of the one or more images having hairs that have been treated with a light pulse. These embodiments provide the subject or other user of the treatment device with feedback that enables them to identify where light pulses should be applied and thereby improve the coverage of the treatment operation over the skin.

In some embodiments the apparatus further comprises a user interface configured to receive the first signal, and the first signal is configured to cause the user interface to output feedback to a user of the treatment device on whether the hairs on the first area of the skin have been treated with a light pulse. These embodiments also provide the subject or other user of the treatment device with feedback that enables them to identify where light pulses should be applied and thereby improve the coverage of the treatment operation over the skin.

In some embodiments the first signal is output to a control unit of the treatment device, and the control unit is configured to determine whether the treatment device should apply a light pulse to the first area of the skin based on the first signal. Thus, these embodiments are useful where the application of light pulses to the skin is controlled automatically so that coverage of the treatment operation over the skin can be improved.

According to a second aspect, there is provided a system that comprises an imaging unit arranged to obtain images of skin of a subject; and an apparatus according to the first aspect or any embodiment thereof.

In some embodiments the imaging unit comprises at least a first imaging component for obtaining one or more images of the skin of the subject. In these embodiments the imaging unit can further comprise a first polariser arranged with respect to the first imaging component such that light incident on to the first imaging component passes through the first polariser. The use of a polariser can improve the depth of the skin area visible in the image (i.e. a polariser enables light to be observed at different penetration depths in the skin).

In some embodiments the system further comprises a treatment device that is configured to apply a light pulse to the skin of the subject to perform a treatment operation to hairs on the skin. In these embodiments the treatment device comprises the imaging unit and/or the apparatus. In alternative embodiments the treatment device is separate from the apparatus.

According to a third aspect, there is provided a computer-implemented method for determining whether hairs on an area of skin of a subject have been treated with a light pulse from a treatment device. The treatment device is configured to apply a light pulse to skin of a subject to perform a treatment operation to hairs on the skin. The method comprises receiving one or more images of a first area of the skin from an imaging unit, wherein the imaging unit is arranged to obtain images of the skin of the subject; processing the one or more images to determine whether the hairs on the first area of the skin have been treated with a light pulse based on a degree of at least one of carbonisation and curling of the hairs on the first area of the skin as shown in the one or more images; and outputting a first signal indicating whether the hairs on the first area of skin have been treated with a light pulse. Thus, the method is able to determine whether hairs on an area of skin have been treated with a light pulse from one or more images of the skin area.

In some embodiments the step of processing comprises determining the degree of carbonisation of the hairs based on a colour of the hairs and/or size of the hairs determined from the one or more images. In some embodiments the step of processing comprises determining the degree of curling of the hairs based on a degree of curvature of the hairs determined from the one or more images.

In some embodiments the step of processing comprises comparing the determined degree of said at least one of carbonisation and curling of the hairs on the first area of the skin to respective thresholds for the degree of carbonisation and the degree of curling; or combining the determined degrees of carbonisation and curling of the hairs into a combined degree of carbonisation and curling, and comparing the combined degree of carbonisation and curling to a threshold for the combined degree of carbonisation and curling.

In further or alternative embodiments, the step of processing comprises using a trained machine learning model to process the one or more images to determine whether the hairs on the first area of the skin have been treated with a light pulse. The trained machine learning model can be an artificial neural network, such as a deep neural network.

In some embodiments the method further comprises receiving one or more further images of the first area of the skin from the imaging unit, wherein the one or more further images are obtained by the imaging unit after a light pulse is applied to the first area of the skin; and updating the trained machine learning model using the one or more further images. These embodiments enable the performance of the machine learning model to be refined or improved over time, and in particular the use of images of the subject's skin enables the machine learning model to be calibrated or customized to the skin characteristics of the subject.

In some embodiments the method further comprises analyzing the one or more images to identify parts of the one or more images comprising hairs, and the step of processing comprises processing the identified parts of the one or more images to determine whether the hairs on the first area of the skin have been treated with a light pulse. These embodiments can make the processing of the one or more images more efficient.

In some embodiments the method further comprises processing the one or more images to determine further information about the hairs on the first area of the skin, and including said further information in the first signal. In these embodiments the further information can comprise at least one of a density of the hairs in the first area of the skin; a strength of the hairs in the first area of the skin; a thickness of the hairs in the first area of the skin; and a colour of the hairs in the first area of the skin.

In some embodiments the first signal comprises the one or more images and an indication of a part or parts of the one or more images having hairs that have been treated with a light pulse. These embodiments provide the subject or other user of the treatment device with feedback that enables them to identify where light pulses should be applied and thereby improve the coverage of the treatment operation over the skin.

In some embodiments a user interface receives the first signal, and the first signal causes the user interface to output feedback to a user of the treatment device on whether the hairs on the first area of the skin have been treated with a light pulse. These embodiments also provide the subject or other user of the treatment device with feedback that enables them to identify where light pulses should be applied and thereby improve the coverage of the treatment operation over the skin.

In some embodiments the first signal is output to a control unit of the treatment device, and the control unit determines whether the treatment device should apply a light pulse to the first area of the skin based on the first signal. Thus, these embodiments are useful where the application of light pulses to the skin is controlled automatically so that coverage of the treatment operation over the skin can be improved.

According to a fourth aspect, there is provided an apparatus for training a machine learning model, MLM, for use in determining whether hairs on a first area of skin have been treated with a light pulse. The apparatus comprising a processing unit configured to obtain a plurality of images of skin for one or more test subjects, wherein each image is annotated with an indication of whether hair on the skin in the image has been treated with a light pulse, wherein the plurality of images includes at least one image annotated with an indication that hair on the skin in the image has been treated with a light pulse and at least one image annotated with an indication that hair on the skin in the image has not been treated with a light pulse; and train a MLM using the plurality of images to distinguish between images in which hairs on skin have been treated with a light pulse from images in which hairs on skin that have not been treated with a light pulse based on a degree of at least one of carbonisation and curling of hair shown in the images.

According to a fifth aspect, there is provided an apparatus for using a machine learning model, MLM, that comprises a processing unit is configured to: receive one or more images of areas of skin from an imaging unit, wherein the imaging unit is arranged to obtain images of skin of a subject; use a MLM trained according by an apparatus according to the fourth aspect to analyze the one or more images to determine if hairs on the areas of skin in the one or more images have been treated with a light pulse; and outputting a first signal indicating whether hairs on the areas of skin have been treated with a light pulse.

According to a sixth aspect, there is provided a computer-implemented method of training a machine learning model, MLM, for use in determining whether hairs on a first area of skin have been treated with a light pulse. The method comprises: obtaining a plurality of images of skin for one or more test subjects, wherein each image is annotated with an indication of whether hair on the skin in the image has been treated with a light pulse, wherein the plurality of images includes at least one image annotated with an indication that hair on the skin in the image has been treated with a light pulse and at least one image annotated with an indication that hair on the skin in the image has not been treated with a light pulse; and training a MLM using the plurality of images to distinguish between images in which hairs on skin have been treated with a light pulse from images in which hairs on skin that have not been treated with a light pulse based on a degree of at least one of carbonisation and curling of hair shown in the images.

According to a seventh aspect, there is provided a computer-implemented method of using a machine learning model, MLM, that comprises: receiving one or more images of areas of skin from an imaging unit, wherein the imaging unit is arranged to obtain images of skin of a subject; using a MLM trained according to the method of the sixth aspect to analyze the one or more images to determine if hairs on the areas of skin in the one or more images have been treated with a light pulse; and outputting a first signal indicating whether hairs on the areas of skin have been treated with a light pulse.

According to an eighth aspect, there is provided a computer program product comprising a computer readable medium having computer readable code embodied therein, the computer readable code being configured such that, on execution by a suitable computer or processing unit, the computer or processing unit is caused to perform the method according to the third aspect, the sixth aspect, the seventh aspect, or any embodiment thereof.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF THE EMBODIMENTS

As noted above, the techniques described herein can be used to determine whether hairs on an area of skin have been treated with a light pulse from a treatment device. The techniques can be implemented by the treatment device (e.g. by a processing unit in the treatment device), or implemented by a processing unit in a separate apparatus. An imaging unit (e.g. a camera) is required in order to obtain one or more images of an area of skin on a subject. The imaging unit may be part of the treatment device, part of a separate apparatus, or separate from both the treatment device and any apparatus that implements the techniques described herein.

Figure 1:
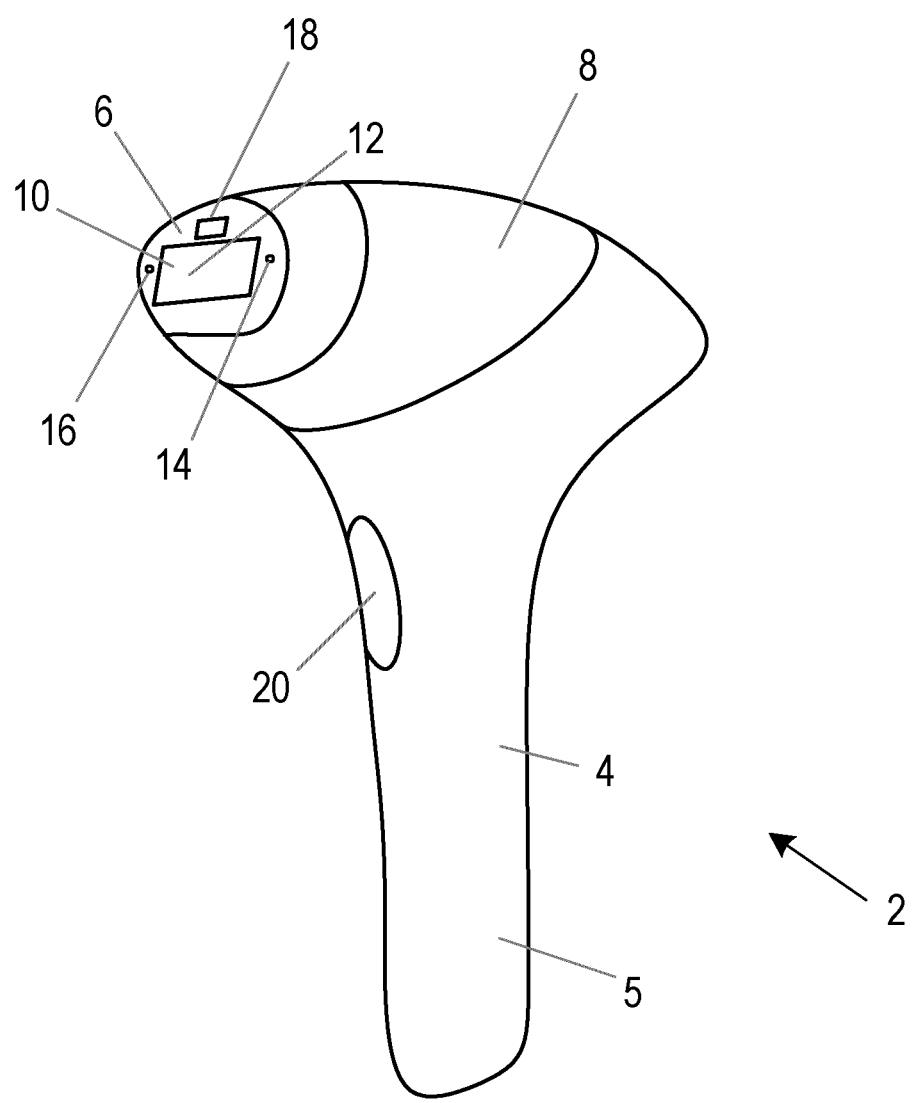
FIG. 1 is an illustration of an exemplary treatment device with which the invention can be used.

FIG. 1 is an illustration of an exemplary treatment device 2 that can be used to apply a light pulse to an area of skin. It will be appreciated that the treatment device 2 in FIG. 1 is merely presented as an example of a hand-held treatment device 2 that the invention can be used with, and the treatment device 2 is not limited to the form shown in FIG. 1 or to being a hand-held treatment device. The treatment device 2 is for use on a body of a subject (e.g. a person or an animal), and is to be held in one or both hands of a user during use. The treatment device 2 is to perform some treatment operation to hairs on the body of the subject using one or more light pulses when the treatment device 2 is in contact with a body part of the subject. The treatment operation can be removal of unwanted hairs by laser and/or light therapies (known as a photoepilation treatment or Intense Pulsed Light, IPL, treatment).

As described herein, the treatment device 2 is operated or used by a 'user', and the treatment device 2 is used on a body of a 'subject'. In some cases the user and the subject is the same person, i.e. the treatment device 2 is held in a hand and used by a user on themselves (e.g. used on the skin on their leg). In other cases the user and the subject are different people, e.g. the treatment device 2 is held in a hand and used by a user on someone else. In either case, it is difficult for a user to achieve complete coverage of the body region and/or avoid over-treating certain areas of the body region since there are little or no user-perceptible changes to the skin or hairs shortly after applying a light pulse.

The exemplary treatment device 2 comprises a housing 4 that includes at least a handle portion 5 and a head portion 6. The handle portion 5 is shaped to enable the user to hold the treatment device 2 with one hand. The head portion 6 is at a head end 8 of the housing 4, and the head portion 6 is to be placed into contact with the subject in order for the personal care operation to be performed on the body or skin of the subject at the position that the head portion 6 is in contact with the body or skin.

The treatment device 2 is for performing a treatment operation using light pulses. Thus, in FIG. 1 the head portion 6 comprises an aperture 10 is arranged in or on the housing 4 so that the aperture 10 can be placed adjacent to or on (i.e. in contact with) the skin of the subject. The treatment device 2 includes one or more light sources 12 that are for generating light pulses that are to be applied to the skin of the subject via the aperture 10 and effect a treatment operation. The one or more light sources 12 are arranged in the housing 4 so that the light pulses are provided from the one or more light sources 12 through the aperture 10. The aperture 10 may be in the form of an opening at the head end 8 of the housing 4, or it may be in the form of a window (including a waveguide) that is transparent or semi-transparent to the light pulses (i.e. the light pulses can pass through the window).

In the exemplary embodiment shown in FIG. 1, the aperture 10 has a generally rectangular shape, which results in a generally rectangular-shaped skin treatment region on the skin. It will be appreciated that the aperture 10 can have any other desired shape. For example the aperture 10 can be square, elliptical, circular, or any other polygonal shape.

The one or more light sources 12 can generate light pulses of any suitable or desired wavelength (or range of wavelengths) and/or intensities. For example, the light source 12 can generate visible light, infra-red (IR) light and/or ultra-violet (UV) light. Each light source 12 can comprise any suitable type of light source, such as one or more light emitting diodes (LEDs), a (Xenon) flash lamp, a laser or lasers, etc. The light source(s) 12 can provide light pulses with spectral content in the 560-1200 nanometre (nm) range for a duration of around 2.5 milliseconds (ms), as these wavelengths heat melanin in the hair and hair root by absorption, which puts the hair follicles in a resting phase, preventing hair regrowth.

The one or more light sources 12 are configured to provide pulses of light. That is, the light source(s) 12 are configured to generate light at a high intensity for a short duration (e.g. less than 1 second). The intensity of the light pulse should be high enough to effect the treatment operation on the skin or body part adjacent the aperture 10.

The illustrated treatment device 2 also includes two skin contact sensors 14, 16 positioned on or in the head portion 6 that are used to determine whether the head portion 6 is in contact with the skin. The skin contact sensors 14, 16 measure a parameter that is indicative of whether the head portion 6 is in contact with skin, and generate respective measurement signals that comprise a time-series of measurements of the parameter. The measurement signals can be processed to determine if the head portion 6 is in contact with skin. Typically a skin contact sensor is used in a treatment device 2, particularly a photoepilator, to make sure that the treatment device 2 is correctly in contact with skin before a light pulse is generated to avoid the light pulse being directed into the eyes of the user or subject.

In some embodiments the parameter can be capacitance, and so the skin contact sensors 14, 16 can measure capacitance via a respective pair of electrical contacts or electrodes on the surface of the head portion 6, with the measured capacitance being indicative of whether there is skin contact. In alternative embodiments, the parameter can be an intensity or level of light, and so the skin contact sensors 14, 16 can be light sensors that measure an intensity or level of light incident on the light sensor, with the measured intensity or level being indicative of whether there is skin contact (e.g. less/no light could indicate skin contact as the skin obscures the light sensors 14, 16, and vice versa). In other alternative embodiments, the parameter can be a measure of contact pressure, and so the skin contact sensors 14, 16 can measure contact pressure via respective pressure sensors or mechanical switches, with the measured contact pressure being indicative of whether there is skin contact.

The illustrated treatment device 2 also includes a skin tone sensor 18 positioned on or in the head portion 6 that is used to determine a skin tone of the skin that the head portion 6 is in contact with. The skin tone sensor 18 measures a parameter that is indicative of the skin tone of the skin, and generates a measurement signal that comprises a time-series of measurements of the parameter. The measurement signal can be processed to determine the skin tone of the skin that the head portion 6 is in contact with. Typically a skin tone sensor is used in a treatment device 2, particularly a photoepilator, to make sure that the light pulse has an intensity that is appropriate for the type of skin being treated, or even to prevent a light pulse being generated if the skin type is unsuitable for light pulses (e.g. darker skin which has a much higher melanin content).

In some embodiments the skin tone sensor 18 can be a light sensor and the parameter measured by the light sensor can be an intensity or level of light at a particular wavelength or multiple wavelengths reflected from the skin. The measured intensity or level of reflected light at a particular wavelength(s) can be indicative of the skin tone. The measured intensity or level of reflected light can be based on the concentration of melanin in the skin, and thus the measured intensity or level can indicate the melanin concentration. The melanin concentration can be derived, for example, from measurements of light reflection at 660 nm (red) and 880 nm (infrared) wavelengths.

The illustrated treatment device 2 also includes a user control 20 that can be operated by the user to activate the treatment device 2 so that the head portion 6 performs the required treatment operation on the body of the subject (e.g. the generation of one or more light pulses by the one or more light source(s) 12). The user control 20 may be in the form of a switch, a button, a touch pad, etc.

Figure 2:
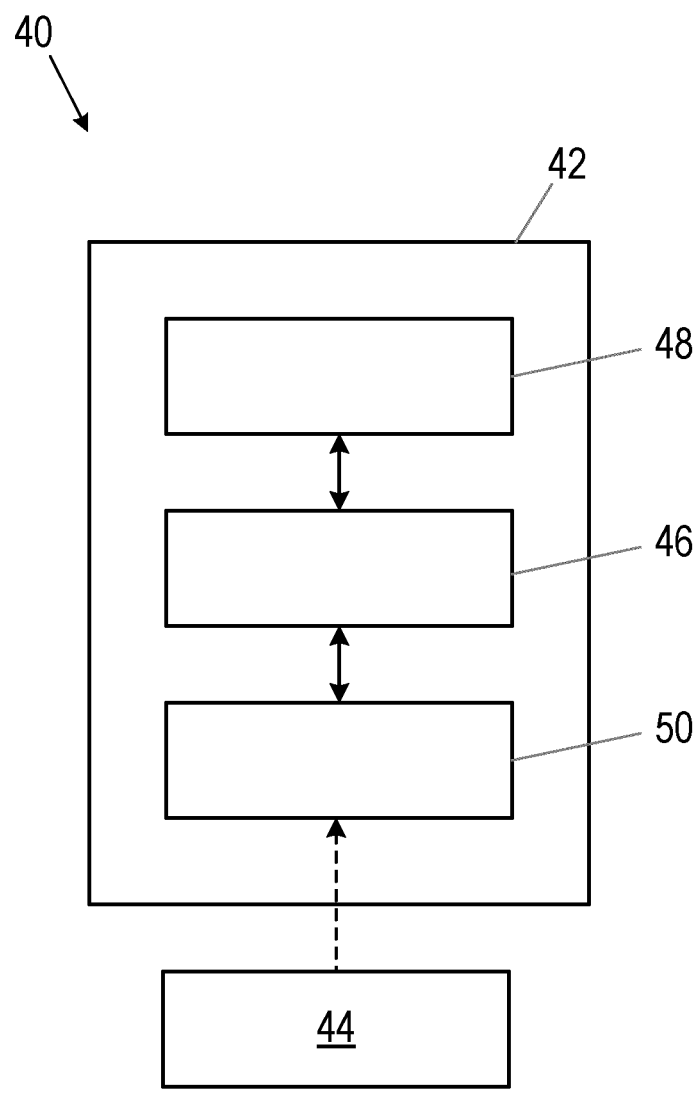
FIG. 2 is a block diagram of an exemplary system comprising an imaging unit and an apparatus according to various embodiments.

FIG. 2 is a block diagram of an exemplary system 40 comprising an apparatus 42 for determining whether hairs on an area of skin have been treated with a light pulse and an imaging unit 44. In some implementations the treatment device 2 can be considered part of the system 40, although the treatment device 2 is not shown in FIG. 2. As noted above, the apparatus 42 can be a separate device to the treatment device 2, and thus the apparatus 42 may be in the form of an electronic device, such as a smart phone, smart watch, tablet, personal digital assistant (PDA), laptop, desktop computer, remote server, smart mirror, etc. In other embodiments, the apparatus 42, and particularly the functionality according to the invention provided by the apparatus 42, is part of the treatment device 2.

The imaging unit 44 is provided to generate one or more images (or a video sequence) of one or more areas of skin of the subject where a light pulse may or may not have been applied. The imaging unit 44 may include any suitable components for capturing an image, for example a charge-coupled device (CCD) and one or more lenses and/or mirrors. In some embodiments, the imaging unit 44 is a camera, such as a digital camera. In some embodiments, one or more additional optical components are associated with the imaging unit 44, such as a polariser that is placed in front of the imaging unit 44 in order to polarize light that is incident on the imaging unit 44. The use of a polariser can improve the depth of the skin area visible in the image (i.e. a polariser enables light to be observed at different penetration depths in the skin).

The imaging unit 44 is shown in FIG. 2 as being separate from the apparatus 42, but it will be appreciated that in other embodiments the imaging unit 44 can be integral with or part of the apparatus 42. In embodiments where the imaging unit 44 is separate from the apparatus 42, the imaging unit 44 may be part of the treatment device 2, or it may also be separate from the treatment device 2. In embodiments where the imaging unit 44 is part of the treatment device 2, the imaging unit 44 can be arranged in the treatment device 2 close to the aperture 10 so that images can be obtained when the treatment device 2 is on or close to the skin.

The apparatus 42 comprises a processing unit 46 that generally controls the operation of the apparatus 42 and enables the apparatus 42 to perform the method and techniques described herein. Briefly, the processing unit 44 receives one or more images from the imaging unit 44, processes the image(s) to determine whether hairs on an area of skin shown in the image(s) have been treated with a light pulse and output a signal indicating whether hairs on the area of skin have been treated with a light pulse.

Thus the processing unit 46 can be configured to receive the image(s) from the imaging unit 44, either directly in embodiments where the imaging unit 44 is part of the apparatus 42, or via another component in embodiments where the imaging unit 44 is separate from the apparatus 42. In either case, the processing unit 46 can include or comprise one or more input ports or wires for receiving the images (or signals carrying information representing the image(s)) from the imaging unit 44 or the other component as appropriate. The processing unit 46 can also include or comprise one or more output ports or wires for outputting the signal indicating whether hairs on the area of skin have been treated with a light pulse.

The processing unit 46 can be implemented in numerous ways, with software and/or hardware, to perform the various functions described herein. The processing unit 46 may comprise one or more microprocessors or digital signal processors (DSPs) that may be programmed using software or computer program code to perform the required functions and/or to control components of the processing unit 46 to effect the required functions. The processing unit 46 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

The processing unit 46 can comprise or be associated with a memory unit 48. The memory unit 48 can store data, information and/or signals (including image(s)) for use by the processing unit 46 in controlling the operation of the apparatus 42 and/or in executing or performing the methods described herein. In some implementations the memory unit 48 stores computer-readable code that can be executed by the processing unit 46 so that the processing unit 46 performs one or more functions, including the methods described herein. In particular embodiments, the program code can be in the form of an application for a smart phone, tablet, laptop, computer or server. The memory unit 48 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EEPROM), and the memory unit can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In the embodiment shown in FIG. 2, as the apparatus 42 is shown as being separate from the imaging unit 44, the apparatus 42 also includes interface circuitry 50 to enable the apparatus 42 to receive the image(s) from the imaging unit 44. The interface circuitry 50 in the apparatus 42 enables a data connection to and/or data exchange with other devices, including any one or more of the imaging unit 44, the treatment device 2, servers, databases, user devices, and sensors. The connection to the imaging unit 44 (or any electronic device, such as treatment device 2) may be direct or indirect (e.g. via the Internet), and thus the interface circuitry 50 can enable a connection between the apparatus 42 and a network, or directly between the apparatus 42 and another device (such as imaging unit 44 and/or treatment device 2), via any desirable wired or wireless communication protocol. For example, the interface circuitry 50 can operate using WiFi, Bluetooth, Zigbee, or any cellular communication protocol (including but not limited to Global System for Mobile Communications (GSM), Universal Mobile Telecommunications System (UMTS), Long Term Evolution (LTE), LTE-Advanced, etc.). In the case of a wireless connection, the interface circuitry 50 (and thus apparatus 42) may include one or more suitable antennas for transmitting/receiving over a transmission medium (e.g. the air). Alternatively, in the case of a wireless connection, the interface circuitry 50 may include means (e.g. a connector or plug) to enable the interface circuitry 50 to be connected to one or more suitable antennas external to the apparatus 42 for transmitting/receiving over a transmission medium (e.g. the air). The interface circuitry 50 is connected to the processing unit 46.

Although not shown in FIG. 2, the apparatus 42 may comprise one or more user interface components that includes one or more components that enables a user of apparatus 42 to input information, data and/or commands into the apparatus 42, and/or enables the apparatus 42 to output information or data to the user of the apparatus 42. The user interface can comprise any suitable input component(s), including but not limited to a keyboard, keypad, one or more buttons, switches or dials, a mouse, a track pad, a touchscreen, a stylus, a camera, a microphone, etc., and the user interface can comprise any suitable output component(s), including but not limited to a display unit or display screen, one or more lights or light elements, one or more loudspeakers, a vibrating element, etc.

It will be appreciated that a practical implementation of an apparatus 42 may include additional components to those shown in FIG. 2. For example the apparatus 42 may also include a power supply, such as a battery, or components for enabling the apparatus 42 to be connected to a mains power supply.

As noted above, the techniques described herein aim to provide a way to determine whether hairs on an area of skin have been treated with a light pulse. In particular, it has been found that after a suitable light pulse is applied (i.e. at the appropriate intensity and/or wavelength), the carbonisation of the hairs increases and/or the amount of curl in the hairs increases. Hair consists of keratin held together by disulphide bonds. When the light pulse is applied, these disulphide bonds are broken. When these bonds are broken, the colour appearance and structural integrity of the hair changes, leading to the hair 'curling up' and thus the curvature of the hairs increasing. This is the carbonisation and curling effect.

Figure 3:
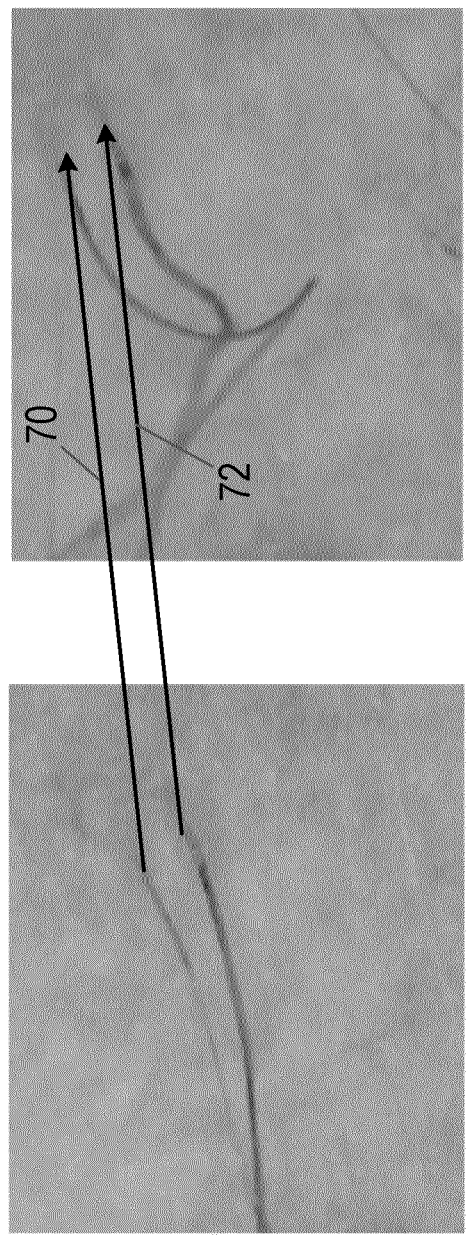
FIGS. 3-5 show several examples of carbonisation and curling of hair before and after a light pulse is applied.
Figure 4:
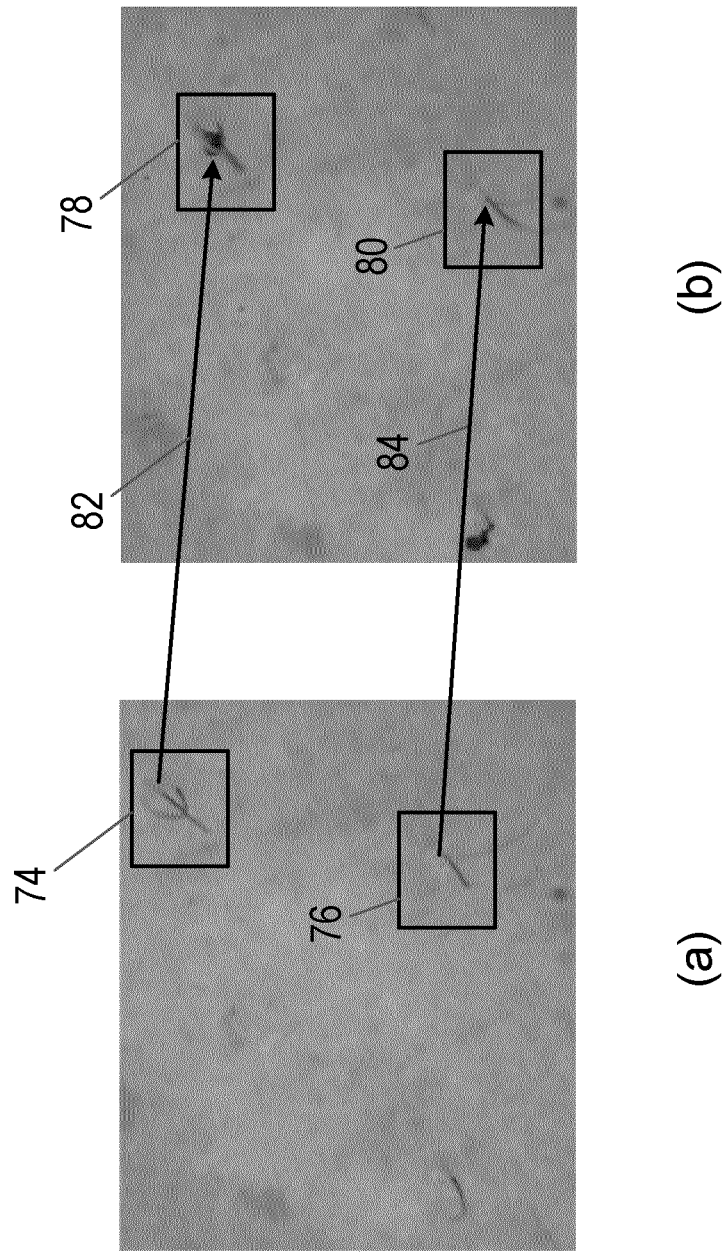
Figure 5:
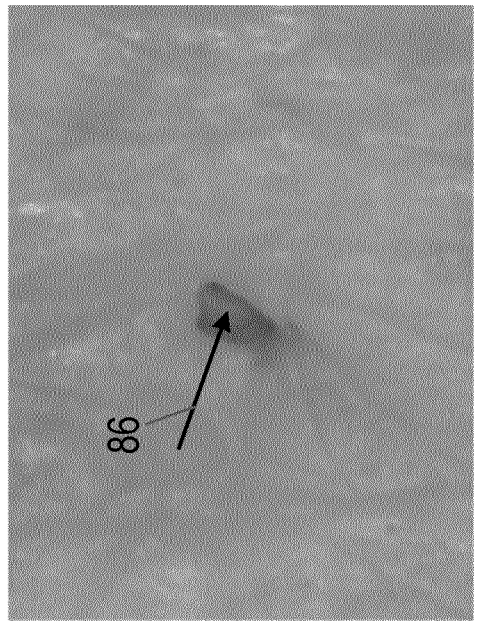
Figure 5:
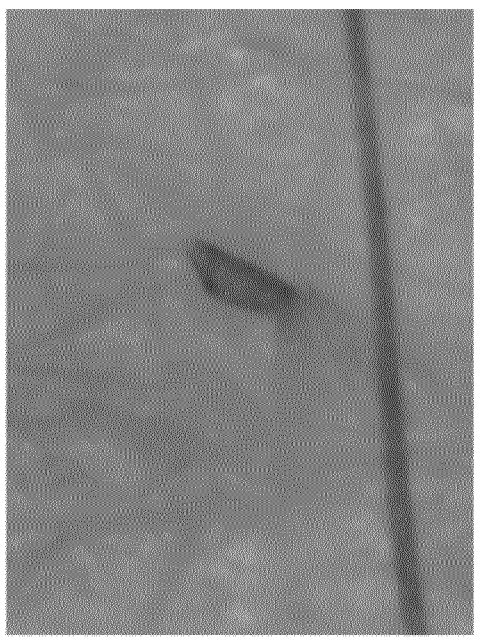
Figure 5:
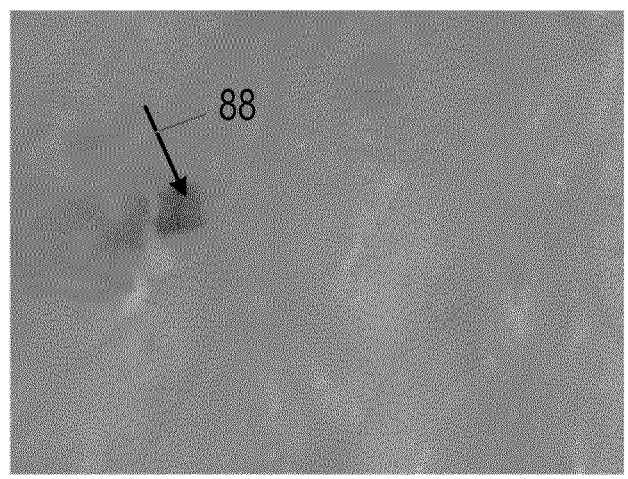
Figure 5:
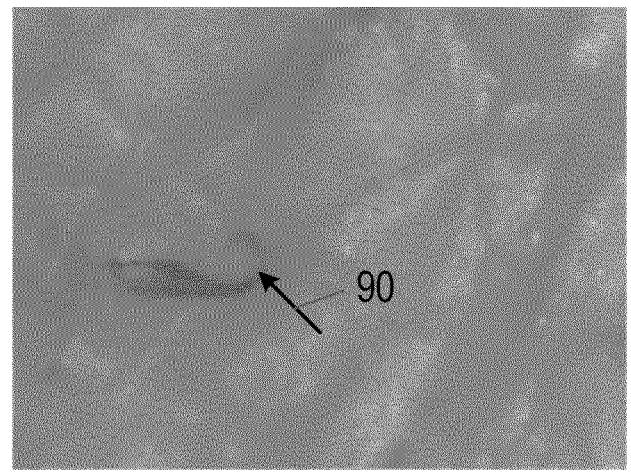
Figure 5:
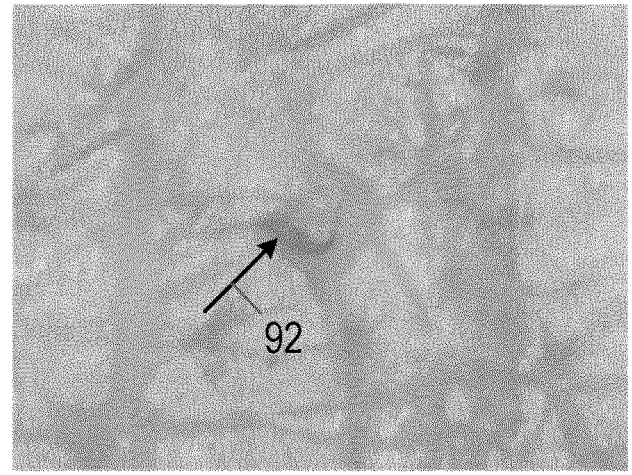

FIGS. 3-5 show several examples of carbonisation and curling of hair before and after a light pulse is applied.

FIG. 3(a) is an image of an area of skin that has some unshaven hairs before a light pulse is applied. Two hairs are visible in FIG. 3(a). FIG. 3(b) is an image of the same area of skin after a light pulse has been applied, and the arrows 70, 72 show how the hairs visible in FIG. 3(a) pair up with the hairs in FIG. 3(b). It can be seen that the appearance of the two hairs has changed after the application of the light pulse, with the amount of visible carbonisation increased in FIG. 3(b) relative to FIG. 3(a), i.e. the hairs appear darker and thicker in FIG. 3(b) relative to their appearance in FIG. 3(a). In addition, the hairs are more curled in FIG. 3(b) compared to before the light pulse is applied. The images in FIGS. 3(a) and (b) were obtained using an imaging unit 44 and a polariser placed in front of the imaging unit 44.

FIG. 4(a) is an image of an area of skin that has some trimmed hairs (i.e. the hairs are short, but not cut at the level of the skin) before a light pulse is applied. Two groups of hairs are highlighted in FIG. 4(a) by boxes 74, 76. FIG. 4(b) is an image of the same area of skin after a light pulse has been applied, and the boxes 78, 80 (with the correspondence between the hairs in the two images being shown by arrows 70, 72). It can be seen that the appearance of the hairs has changed after the application of the light pulse, with the amount of visible carbonisation in FIG. 4(b) increased relative to FIG. 4(a). In addition, the hairs are slightly more curled in FIG. 4(b) compared to before the light pulse is applied. The images in FIGS. 4(a) and (b) were obtained using an imaging unit 44 and a polariser placed in front of the imaging unit 44.

FIG. 5(a) is an image of an area of skin that has some shaved hairs (i.e. the hairs are short and cut to approximately the level of the skin) before a light pulse is applied. A hair is visible in FIG. 5(a). FIG. 5(b) is an image of the same area of skin after a light pulse has been applied, and the hair is indicated by arrow 86. It can be seen that the appearance of the hair has changed after the application of the light pulse, with the amount of visible carbonisation increased in FIG. 5(b) relative to FIG. 5(a). As the hair is already quite short, curling of the hair is unlikely, and there is little visible difference in the curling of the hair due to the light pulse. As the hairs are quite short in this example, the images in FIGS. 5(a) and (b) were obtained using an imaging unit 44 having a zoom or other form of magnification of the imaged area.

FIGS. 5(c) to 5(e) are images of other areas of skin after a light pulse has been applied, with hairs being indicated in each image by arrows 88, 90 and 92 respectively. It can be seen in each image that the hair shows relatively high levels of carbonisation. In FIGS. 5(d) and (e), curling of the hair is visible. As with FIGS. 5(a) and 5(b), the hairs are quite short in these examples, so the images in FIG. 5(c)-(e) were obtained using an imaging unit 44 having a zoom or other form of magnification of the imaged area.

Thus, from FIGS. 3-5, it can be seen that the degree (i.e. amount) of carbonisation and/or curling of the hairs can indicate whether hairs on an area of skin have been treated with a light pulse, and suitable processing of the image(s) can determine whether hairs on an area of skin have been treated with a light pulse based on the degree of carbonisation and/or degree of curl.

Figure 6:
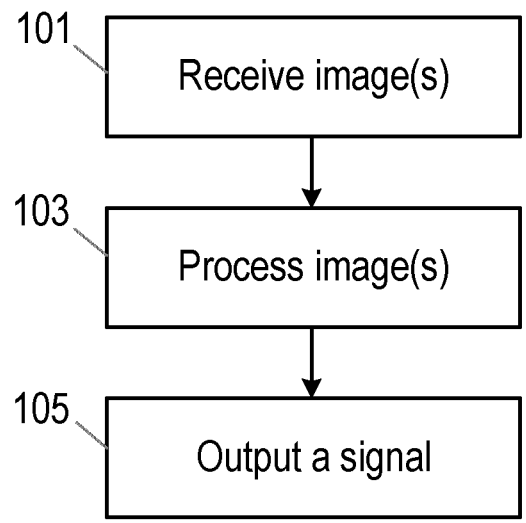
FIG. 6 is a flow chart illustrating an exemplary method of determining whether hairs on a first area of skin have been treated with a light pulse.

The flow chart in FIG. 6 illustrates an exemplary method according to the techniques described herein for determining whether hairs on an area of skin have been treated with a light pulse. One or more of the steps of the method can be performed by the processing unit 46 in the apparatus 42, in conjunction with either of the memory unit 48 and interface circuitry 50 of the apparatus 42, and/or the imaging unit 44, as appropriate. The processing unit 46 may perform the one or more steps in response to executing computer program code that can be stored on a computer readable medium, such as, for example, the memory unit 48.

In step 101, one or more images of a first area of skin are received. The image(s) can be received directly from imaging unit 44, for example in real-time or near real-time as the images are generated by the imaging unit 44. Alternatively, the image(s) may have been previously generated by the imaging unit 44 and stored for subsequent analysis, for example in the memory unit 48, in a memory unit associated with the treatment device 2 or imaging unit 44, or in a remote database, in which case step 101 can comprise the processing unit 46 obtaining or retrieving the image(s) from the storage location (e.g. from memory unit 48, etc.).

In step 103, the one or more images are processed to determine whether the hairs on the first area of skin have been treated with a light pulse. The decision on whether hairs have been treated is based on a degree of at least one of carbonisation and curling of hairs shown in the image(s). The carbonisation of hair relates to the colour of the hair and/or size of the hair shown in the image(s). The curling of the hair relates to the amount of curvature of the hairs shown in the image(s).

In some embodiments, as part of step 103, the one or more images can be analyzed to identify parts of the image(s) that comprise hairs, and the processing to determine whether hairs on the first area of skin have been treated with a light pulse can operate on the identified parts of the image(s). The output of this analysis can be a mask (image mask) or a similar indication highlighting the part(s) of the image that contain hairs (or conversely that do not contain hairs). This analysis of the image(s) can comprise using contour detection and/or edge detection image processing techniques (which are known to those skilled in the art) to detect the hairs in the image. For example edge detection techniques can detect the outline of the hairs in the image.

Then, in step 105, a signal is output indicating whether the hairs on the first area of skin have been treated with a light pulse. In some embodiments the indication can be a simple 'skin area treated' or 'skin area not treated'. In other or further embodiments, the indication can include additional information relating to the skin, hair or applied treatment.

The signal may be provided to a user interface component of the apparatus 42 or treatment device 2 and the signal is configured to cause the user interface component to indicate whether the hairs on the area of skin have been treated with a light pulse. For example, the signal could cause a red light on the treatment device 2 to be illuminated if it is determined that the area of skin currently in view of the imaging unit 44, and which could be treated with a light pulse, has already been treated with a light pulse. Likewise the signal could cause a green light on the treatment device 2 to be illuminated if it is determined that the area of skin currently in view of the imaging unit 44 has not been treated with a light pulse. The user of the treatment device 2 would be able to use these indications to determine whether to trigger a light pulse at the current position of the treatment device 2, which can help the user to improve the coverage of the treatment operation over the skin of the subject. As another example, the user can use the indication to determine whether a previous light pulse treatment on this part of the skin was successful. As another example, where the apparatus 42 is in the form of a smartphone or similar type of device, the feedback on whether the area of skin has been treated with a light pulse can be provided to the user or subject via an app (software application) executing on the apparatus 42. Those skilled in the art will be aware of other ways in which feedback on whether the area of skin has been treated with a light pulse can be provided to a user, e.g. including using a display screen, a loudspeaker, haptic feedback, etc.

Alternatively (or in addition), where the treatment device 2 can automatically trigger a light pulse if the conditions are suitable (e.g. the treatment device 2 is in contact with skin, the tone of the skin the treatment device 2 is in contact with is suitable to receive a light pulse, etc.), the signal can be provided to a control unit of the treatment device 2, and the control unit can use the signal as part of taking the decision on whether to treat the area of skin currently adjacent to the aperture 10 with a light pulse.

The signal output in step 105 can also include information about the hairs on the first area of skin. The information can be determined during the processing of the image(s) in step 103. The information may be used by a user or by a control unit in the treatment device 2 as part of making a decision on whether to trigger a light pulse at the current location of the treatment device 2 on the skin. The information may be provided as a value, a percentage or a combination thereof. In some embodiments, the information comprises at least one of a density of the hairs in the first area of skin, a strength of the hairs in the first area of skin, a thickness of the hairs in the first area of skin and a colour of the hairs in the first area of skin. The colour of the hairs can be determined from the degree of carbonisation of the hairs and degree of hair curling in response to an applied light pulse, since there are variations in the amount of hair carbonisation and hair curling in response to a light pulse over hair with different colours. The degree (amount) of carbonisation of an individual hair (e.g. 50% carbonized) can provide an indication of the thickness and/or strength of the hair. Information on the hair density can be determined by analyzing the amount of hairs that are visible in the image(s).

Any of these types of information may be useful in determining a suitable setting for the treatment device 2 to use to trigger the light pulse, for example an intensity setting could be adjusted based on the hair thickness, or a wavelength of the light pulse could be adjusted based on the colour of the hair.

In some embodiments, the signal output in step 105 can include one or more of the image(s) received in step 101. The output image(s) may include an indication (e.g. in the form of a mask on the image) of a part or parts of the one or more images having hairs that have been treated with a light pulse.

It will be appreciated that an image of an area of skin may include a part of the skin where treatment with a light pulse has been applied and another part of the skin where treatment with a light pulse has not been applied. These different parts can be identified during the processing in step 103, for example by identifying a group of hairs or area of skin in the image that exhibit characteristics (e.g. carbonisation and curling) consistent with the application of a light pulse, and a separate group of hairs or area of skin in the image that exhibit characteristics consistent with no light pulse having been applied. In these embodiments the signal output in step 105 can indicate (or contain information indicating) the part or parts of the area of skin in the image that have been treated with a light pulse and/or the part or parts that have not been treated with a light pulse.

Step 103 can comprise processing the one or more images to determine a degree of the carbonisation and/or curling of hairs on the first area of skin. It can be determined whether the hairs on the first area of skin have been treated with a light pulse based on the determined degrees of carbonisation and/or curling of hair in the first area of skin. The degree of carbonisation and/or curling of hairs can be expressed as respective scores, for example a high score indicating high carbonisation or high curling, and vice versa. In some embodiments, the determined degrees of carbonisation and curling of hair can be compared to respective thresholds. In some embodiments, if both determined degrees exceed the respective thresholds, then it can be determined that hairs on the area of skin have been treated with a light pulse. In other embodiments, it can be determined that hairs on the area of skin have been treated with a light pulse if at least one of the determined degrees exceeds the respective threshold. Alternatively, the degrees of carbonisation and curling of hair in the first area of skin can be combined to form a single combined degree (e.g. a combined score), and that combined degree can be compared to a threshold to determine whether hairs on the area of skin have been treated with a light pulse.

In some embodiments the degree of carbonisation can be defined based on a colour of the hairs, a change of colour of the hairs from a known pre-treatment/pre-light pulse colour, a size of the hairs, and/or a change of size of the hairs from a known pre-treatment/pre-light pulse size, and the degree of carbonisation can be determined from the image(s) by the colour, change of colour, size and/or change of size of hairs shown in the image(s). The degree of carbonisation of a hairs can be determined from the number of pixels in the image relating to the hairs, or relating to carbonized parts of the hairs (where the carbonized parts can be identified from the colour of those pixels).

In some embodiments the degree of curling can be defined based on a curvature of the hairs and/or a change of curvature of the hairs from a known pre-treatment/pre-light pulse curvature, and the degree of curvature can be determined from the image(s) by the curvature, and/or change of curvature of hairs shown in the image(s).

In other embodiments of step 103, a trained machine learning model (MLM) is used to process the one or more images to determine whether the hairs on the first area of skin have been treated with a light pulse. The MLM can be any suitable type of MLM, for example a classical machine learning model such as feature extraction with support vector machines, decision trees, random forests, etc., . . . , or an artificial neural network, such as a deep neural network, that has multiple layers between input and output layers and which identifies a linear or non-linear relationship between the input and output layers. The MLM makes an evaluation for each image to classify whether the hairs on the skin area shown in the image has been treated with a light pulse or not. In some embodiments the MLM directly receives the image(s) and performs all required analysis and processing of the images (e.g. determine a degree of carbonisation and/or a degree of curling) in order to determine whether hairs on the area of skin visible in the image have been treated with a light pulse. This is particularly the case for a MLM that is an artificial neural network, such as a deep neural network. In other embodiments, for example in the case of the use of a classical MLM, the image(s) can be processed before being provided to the MLM, for example to determine values for the degree of carbonisation and/or degree of curling, and these degrees can be provided to the MLM for analysis (optionally in addition to the image(s)) to determine whether hairs on the area of skin visible in the image have been treated with a light pulse.

Figure 7:
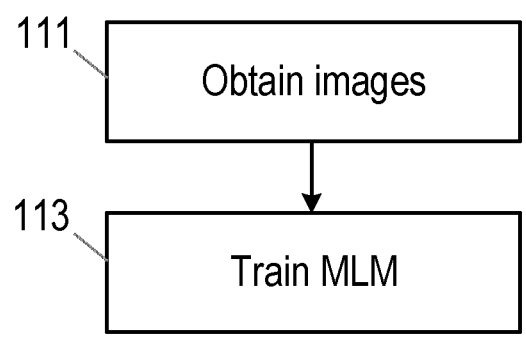
FIG. 7 is a flow chart illustrating a method of training a machine learning model for use in determining whether hairs on a first area of skin have been treated with a light pulse.

The MLM used in embodiments of step 103 will be trained prior to use by the user/subject. The flow chart in FIG. 7 illustrates a method of training a MLM for use in determining whether hairs on an area of skin have been treated with a light pulse. The training method in FIG. 7 may be performed by any suitable apparatus or device, including apparatus 42, although it will be appreciated that the method in FIG. 7 does not need to be performed by the same apparatus or device that performs FIG. 6. For example the training method in FIG. 7 can be performed by a server or computer in a central location, and the trained MLM (or computer code representing the trained MLM) distributed to various apparatus 42 for use in determining whether hairs on an area of skin have been treated with a light pulse according to the method in FIG. 6.

In embodiments where the apparatus 42 implements the method in FIG. 6, one or more of the steps of the method can be performed by the processing unit 46, in conjunction with either of the memory unit 48 and interface circuitry 50 of the apparatus 42, and/or the imaging unit 44, as appropriate. The processing unit 46 may perform the one or more steps in response to executing computer program code that can be stored on a computer readable medium, such as, for example, the memory unit 48.

In order to train the MLM, a training data set is required. The training data set comprises a plurality of images of skin for one or more test subjects (and which may or may not include the subject that the method of FIG. 6 is used on). Each image in the training data set is annotated with an indication of whether hair on the skin in the image has been treated with a light pulse. This annotation may have been made manually by a user or other person. The training data set will include at least one image annotated with an indication that hair on the skin in the image has been treated with a light pulse and at least one image annotated with an indication that hair on the skin in the image has not been treated with a light pulse. It will be appreciated that the larger the training data set, the more accurate the resulting MLM is likely to be. In some embodiments, the images in the training data set can be annotated with additional information, such as the hair count (i.e. number of hairs in the image), the hair thickness or hair density, a degree (e.g. percentage) of carbonisation, or any combination thereof. Preferably, for the trained MLM to be accurate across a range of subjects and hair types, the training data set should include images of hairs that have different levels of hair response to light pulses, for example hairs of different colours.

The training data set is obtained in step 111 of FIG. 7. This step can comprise collecting the images and associated annotations (e.g. using an imaging unit and user interface), or retrieving the images for the training data set from a database or other electronic storage device.

Next, in step 113, an MLM is trained using the plurality of images in the training data set so that the MLM is able to distinguish between images in which hairs on skin have been treated with a light pulse from images in which hairs on skin that have not been treated with a light pulse. The MLM is trained to distinguish between the images based on an degree of carbonisation and curling of hair shown in the images. Where the training data set includes annotations relating to the hair count, the hair thickness, the hair density, and/or the percentage carbonisation, the MLM may also be trained to provide indications of these parameters for an input image. Techniques for training Mom's using a training data set are known to those skilled in the art, and details are not provided herein. Nevertheless, as one example, the MLM can be trained using cross-validation where the MLM is trained using a subset of the images in the training data set and the trained MLM is tested for accuracy using the one or more of the other images in the training data set. This training and testing can be repeated for different subsets of the images in the training data set in order to arrive at the final trained MLM. The trained MLM can then be used in step 103 of FIG. 6.

In some embodiments, once the MLM is deployed and in use by a particular subject, the accuracy of the MLM can be improved or customized to the skin/hair characteristics of the particular subject by updating the MLM using images of the skin of the subject that have been manually or automatically annotated to confirm whether or not a light pulse has been applied. Alternatively or in addition, if the imaging unit 44 is part of the treatment device 2, the imaging unit 44 could be controlled to obtain an image of an area of skin just after the treatment device has applied a light pulse to that area of skin.

The updating (or retraining) of the MLM can be implemented by adding the subject's images to the training data set and retraining the MLM using the updated training data set. In some embodiments this updating or retraining can be performed as part of a calibration procedure for the MLM when a subject first starts to use the apparatus 42.

There is therefore provided improvements in determining whether hairs on an area of skin have been treated with a light pulse.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for use with a treatment device, wherein the treatment device is configured to apply a light pulse to skin of a subject to perform a treatment operation to hairs on the skin, the apparatus comprising a processing unit configured to:
receive one or more images of an area of the skin from an imaging unit, wherein the imaging unit is arranged to obtain images of the skin of the subject;
process the one or more images to determine whether the hairs on the area of the skin have been treated with a light pulse based on a degree of at least one of carbonization of the hairs and/or curling of the hairs on the area of the skin as shown in the one or more images; and
output a signal indicating whether the hairs on the area of the skin have been treated with the light pulse.

2. The apparatus as claimed in claim 1, wherein the processing unit is further configured to determine the degree of carbonization of the hairs based on a color of the hairs and/or a size of the hairs determined from the one or more images.

3. The apparatus as claimed in claim 1, wherein the processing unit is configured to determine the degree of curling of the hairs based on a degree of curvature of the hairs determined from the one or more images.

4. The apparatus as claimed in claim 1, wherein:
the processing unit is further configured to determine a degree of carbonization of the hairs based on a color of the hairs and/or a size of the hairs determined from the one or more images, and/or the processing unit is configured to determine a degree of curling of the hairs based on a degree of curvature of the hairs determined from the one or more images,
the processing unit is configured to determine whether the hairs on the area of the skin have been treated with the light pulse by:
comparing the determined degree of carbonization of the hairs on the area of the skin to a threshold for the degree of carbonisation,
comparing the determined degree of curling of the hairs on the area of the skin to a threshold for the degree of curling, and/or
combining the determined degrees of carbonization and curling of the hairs into a combined degree of carbonization and curling, and comparing the combined degree of carbonisation and curling to a threshold for the combined degree of carbonisation and curling.

5. The apparatus as claimed in claim 1, wherein the processing unit is further configured to use a trained machine learning model to process the one or more images to determine whether the hairs on the area of the skin have been treated with the light pulse.

6. The apparatus as claimed in claim 5, wherein the processing unit is further configured to:
receive one or more further images of the area of the skin from the imaging unit, wherein the one or more further images are obtained by the imaging unit after the light pulse is applied to the area of the skin; and
update the trained machine learning model using the one or more further images.

7. The apparatus as claimed in claim 1, wherein the processing unit is further configured to:
analyze the one or more images to identify parts of the one or more images comprising the hairs, and
process the identified parts of the one or more images to determine whether the hairs on the area of the skin have been treated with the light pulse.

8. The apparatus as claimed in claim 1, wherein the processing unit is further configured to process the one or more images to determine further information about the hairs on the area of the skin, and to include said further information in the outputted signal.

9. The apparatus as claimed in claim 8, wherein the further information comprises one or more of:
a density of the hairs in the area of the skin;
a strength of the hairs in the area of the skin;
a thickness of the hairs in the area of the skin; and
a color of the hairs in the area of the skin.

10. The apparatus as claimed in claim 1, wherein the signal comprises the one or more images and an indication of a part or parts of the one or more images having hairs that have been treated with the light pulse.

11. The apparatus as claimed in claim 1, wherein the apparatus further comprises a user interface configured to receive the signal, and wherein the signal is configured to cause the user interface to output feedback to a user of the treatment device about whether the hairs on the area of the skin have been treated with the light pulse.

12. The apparatus as claimed in claim 1, wherein the first signal is output to a control unit of the treatment device, and wherein said control unit is configured to determine whether the treatment device should apply the light pulse to the area of the skin based on the signal.

13. The apparatus as claimed in claim 1, wherein the imaging unit comprises a camera, or a charge-coupled device (CCD).

14. A computer-implemented method for determining whether hairs on an area of skin of a subject have been treated with a light pulse from a treatment device, wherein the treatment device is configured to apply the light pulse to the skin of the subject to perform a treatment operation to the hairs on the skin, wherein the method comprises:
   receiving one or more images of the area of the skin from an imaging unit, wherein the imaging unit is arranged to obtain images of the skin of the subject;
   processing the one or more images to determine whether the hairs on the area of the skin have been treated with the light pulse based on a degree of at least one of carbonization of the hairs and/or curling of the hairs on the area of the skin as shown in the one or more images, wherein the processing of the one or more images comprises using a trained machine learning model (MLM) to analyze the one or more images to determine if the hairs on the area of the skin in the one or more images have been treated with the light pulse;
   outputting a signal indicating whether the hairs on the area of skin have been treated with the light pulse;
   obtaining a plurality of images of skin for one or more test subjects, wherein each image is annotated with an indication of whether hair on the skin in the image has been treated with the light pulse, wherein the plurality of images includes at least a first image annotated with an indication that hair on the skin in the first image has been treated with the light pulse and a second image annotated with an indication that hair on the skin in the second image has not been treated with the light pulse; and
   training the MLM using the plurality of images to distinguish between images in which the hairs on the skin have been treated with the light pulse from images in which the hairs on the skin have not been treated with the light pulse based on the degree of the carbonisation of the hairs and/or the curling of the hairs shown in the plurality of images.

15. The computer-implemented as claimed in claim 14, wherein the method further comprises determining the degree of carbonization of the hairs based on a color of the hairs and/or a size of the hairs determined from the one or more images.

16. The computer-implemented as claimed in claim 14, wherein the method further comprises determining the degree of curling of the hairs based on a degree of curvature of the hairs determined from the one or more images.

17. The computer-implemented as claimed in claim 14, wherein the method further comprises:
   determining a degree of carbonization of the hairs based on a color of the hairs and/or a size of the hairs determined from the one or more images, and/or the processing unit is configured to determine a degree of curling of the hairs based on a degree of curvature of the hairs determined from the one or more images; and
   determining when the hairs on the area of the skin have been treated with the light pulse by: comparing the determined degree of carbonization of the hairs on the area of the skin to a threshold for the degree of carbonisation; comparing the determined degree of curling of the hairs on the area of the skin to a threshold for the degree of curling; and/or combining the determined degrees of carbonization and curling of the hairs into a combined degree of carbonization and curling, and comparing the combined degree of carbonisation and curling to a threshold for the combined degree of carbonisation and curling.

18. The computer-implemented as claimed in claim 17, wherein the method further comprises:
   receiving one or more further images of the area of the skin from the imaging unit, wherein the one or more further images are obtained by the imaging unit after the light pulse is applied to the area of the skin; and
   updating the trained MLM using the one or more further images.

19. The computer implemented method as claimed in claim 14, further comprising training the MLM to process the one or more images to determine whether the hairs on the area of the skin have been treated with the light pulse.

20. A non-transitory computer program product comprising a computer readable medium having computer readable code embodied therein, the computer readable code being configured such that, on execution by a suitable computer or processing unit, the computer or processing unit is caused to perform the method of claim 14.

* * * * *